(12) United States Patent
Nikolic et al.

(10) Patent No.: US 6,852,076 B2
(45) Date of Patent: Feb. 8, 2005

(54) METHOD FOR IMPROVING CARDIAC FUNCTION

(75) Inventors: Serjan D. Nikolic, San Francisco, CA (US); Hugh R. Sharkey, Redwood City, CA (US); Branislav Radovancevic, Houston, TX (US)

(73) Assignee: CardioKinetix, Inc., Redwood City, CA (US)

( * ) Notice: Subject to any disclaimer, the term of this patent is extended or adjusted under 35 U.S.C. 154(b) by 0 days.

(21) Appl. No.: 10/382,962

(22) Filed: Mar. 6, 2003

(65) Prior Publication Data

US 2003/0163191 A1 Aug. 28, 2003

Related U.S. Application Data

(63) Continuation of application No. 10/212,032, filed on Aug. 1, 2002, which is a continuation-in-part of application No. 09/635,511, filed on Aug. 9, 2000, now abandoned.
(60) Provisional application No. 60/147,894, filed on Aug. 9, 1999.

(51) Int. Cl.[7] ............................. A61F 2/00; A61B 17/08
(52) U.S. Cl. ........................................ 600/37; 606/155
(58) Field of Search ..................... 600/37, 16; 606/153, 606/155, 157; 128/898; 623/11.11, 910; 604/500

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,619,246 A | 10/1986 | Molgaard-Nielsen et al. | |
| 4,832,055 A | 5/1989 | Palestrant | |
| 5,385,156 A | 1/1995 | Oliva | |
| 5,496,277 A | 3/1996 | Termin et al. | |
| 5,527,337 A | 6/1996 | Stack et al. | |
| 5,527,338 A | 6/1996 | Purdy | |
| 5,549,621 A | 8/1996 | Bessler et al. | |
| 5,634,936 A | 6/1997 | Linden et al. | |
| 5,634,942 A | 6/1997 | Chevillon et al. | |
| 5,702,343 A | 12/1997 | Alferness | |

(List continued on next page.)

FOREIGN PATENT DOCUMENTS

| | | |
|---|---|---|
| WO | WO 00/27292 | 5/2000 |
| WO | WO 01/78625 A1 | 10/2001 |
| WO | WO 03/07778 A2 | 1/2003 |
| WO | WO 2004/012629 A1 | 2/2004 |

OTHER PUBLICATIONS

Tetsuji Kawata et al., "Systolic and Diastolic Function After Patch Reconstruction of Left Ventricular Aneurysms", Ann. Thorac. Surg. 59, pp. 403–407, 1995.

(List continued on next page.)

*Primary Examiner*—Corrine McDermott
*Assistant Examiner*—Thomas J Sweet
(74) *Attorney, Agent, or Firm*—Edward J. Lynch; Duane Morris LLP (57) ABSTRACT

A method and a device for improving cardiac function are provided. The device is packaged in a collapsed state in an end of a catheter. Portions of a frame construction of the device spring outwardly when the catheter is withdrawn from the device. Anchoring formations on the frame construction secure the frame construction to a myocardium of the heart. A membrane secured to the frame construction then forms a division between volumes of an endocardial cavity of the heart on opposing sides of the membrane.

16 Claims, 12 Drawing Sheets

U.S. PATENT DOCUMENTS

| | | | |
|---|---|---|---|
| 5,791,231 A | | 8/1998 | Cohn et al. |
| 5,797,849 A | | 8/1998 | Vesely et al. |
| 5,797,960 A | | 8/1998 | Stevens et al. |
| 5,829,447 A | | 11/1998 | Stevens et al. |
| 5,833,698 A | | 11/1998 | Hinchliffe et al. |
| 5,836,968 A | | 11/1998 | Simon et al. |
| 5,843,170 A | | 12/1998 | Ahn |
| 5,865,730 A | | 2/1999 | Fox et al. |
| 5,865,791 A | * | 2/1999 | Whayne et al. .............. 604/500 |
| 5,871,017 A | | 2/1999 | Mayer |
| 5,875,782 A | | 3/1999 | Ferrari et al. |
| 5,876,325 A | | 3/1999 | Mizuno et al. |
| 5,876,449 A | | 3/1999 | Starck et al. |
| 5,879,366 A | | 3/1999 | Shaw et al. |
| 5,882,340 A | | 3/1999 | Yoon |
| 5,910,150 A | | 6/1999 | Saadat |
| 5,916,145 A | | 6/1999 | Chu et al. |
| 5,924,424 A | | 7/1999 | Stevens et al. |
| 5,925,076 A | | 7/1999 | Inoue |
| 5,928,260 A | | 7/1999 | Chin et al. |
| 5,961,440 A | | 10/1999 | Schweich, Jr. et al. |
| 5,961,539 A | | 10/1999 | Northup, III et al. |
| 5,984,917 A | * | 11/1999 | Fleischman et al. .......... 606/32 |
| 6,024,096 A | | 2/2000 | Buckberg |
| 6,024,756 A | | 2/2000 | Huebsch et al. |
| 6,045,497 A | * | 4/2000 | Schweich et al. ............. 600/16 |
| 6,059,715 A | * | 5/2000 | Schweich et al. ............. 600/16 |
| 6,076,013 A | | 6/2000 | Brennan et al. |
| 6,077,214 A | | 6/2000 | Mortier et al. |
| 6,077,218 A | | 6/2000 | Alferness |
| 6,093,199 A | | 7/2000 | Brown et al. |
| 6,095,968 A | | 8/2000 | Snyders |
| 6,096,347 A | | 8/2000 | Geddes et al. |
| 6,099,832 A | | 8/2000 | Mickle et al. |
| 6,102,887 A | * | 8/2000 | Altman ........................ 604/22 |
| 6,125,852 A | | 10/2000 | Stevens et al. |
| 6,132,438 A | * | 10/2000 | Fleischman et al. ........ 606/139 |
| 6,152,144 A | * | 11/2000 | Lesh et al. ................... 128/898 |
| 6,161,543 A | | 12/2000 | Cox et al. |
| 6,193,731 B1 | | 2/2001 | Oppelt et al. |
| 6,221,092 B1 | | 4/2001 | Koike et al. |
| 6,231,561 B1 | * | 5/2001 | Frazier et al. ............... 604/500 |
| 6,258,021 B1 | * | 7/2001 | Wilk ........................... 600/16 |
| 6,267,772 B1 | | 7/2001 | Mulhauser et al. |
| 6,290,674 B1 | | 9/2001 | Roue et al. |
| 6,312,446 B1 | | 11/2001 | Huebsch et al. |
| 6,328,727 B1 | | 12/2001 | Frazier et al. |
| 6,334,864 B1 | | 1/2002 | Amplatz et al. |
| 6,343,605 B1 | * | 2/2002 | Lafontaine .................. 128/898 |
| 6,348,068 B1 | | 2/2002 | Campbell et al. |
| 6,355,052 B1 | | 3/2002 | Neuss et al. |
| 6,360,749 B1 | | 3/2002 | Jayaraman |
| 6,364,896 B1 | | 4/2002 | Addis |
| 6,387,042 B1 | | 5/2002 | Herrero |
| 6,419,669 B1 | | 7/2002 | Frazier et al. |
| 6,436,088 B2 | | 8/2002 | Frazier et al. |
| 6,450,171 B1 | | 9/2002 | Buckberg et al. |
| 6,537,198 B1 | * | 3/2003 | Vidlund et al. ............... 600/16 |
| 6,551,303 B1 | * | 4/2003 | Van Tassel et al. ......... 604/508 |
| 6,592,608 B2 | * | 7/2003 | Fisher et al. ................. 606/213 |
| 2001/0014800 A1 | | 8/2001 | Frazier et al. |
| 2001/0019580 A1 | | 9/2001 | Lau et al. |
| 2002/0028981 A1 | | 3/2002 | Lau et al. |
| 2002/0032481 A1 | | 3/2002 | Gabbay |
| 2002/0055767 A1 | | 5/2002 | Forde et al. |
| 2002/0055775 A1 | | 5/2002 | Carpentier et al. |
| 2002/0169359 A1 | | 11/2002 | McCarthy et al. |
| 2002/0188170 A1 | | 12/2002 | Santamore et al. |
| 2003/0149333 A1 | | 8/2003 | Alferness |

OTHER PUBLICATIONS

Vincent Dor, "The Treatment of Refractory Ischemic Ventricular Tachycardia by Endoventricular Patch Plasty Reconstruction of the Left Ventricle", Seminars in Thoracic and Cardiovascular Surgery, vol. 9, No. 2, pp. 146–155, Apr. 1997.

Daniel Giorgio Di Mattia et al., "Surgical treatment of left ventricular post–infarction aneurysm with endoventriculoplasty: late clinical and functional results", European Journal of Cardio–thoracic Surgery 15, pp. 413–419, 1999.

T Katsumata et al., "An objective appraisal of partial left ventriculectomy for heart failure", Journal of Congestive Heart Failure and Circulator Support, pp. 97–106, 1999.

Vincent Dor, "Surgery for left ventricular aneurysm", Current Opinion in Cardiology, Current Science, pp. 773–780, 1990.

Vincent Dor et al., "Ventricular remodeling in coronary artery disease", Current Opinion in Cardiology, Rapid Science Publishers, pp. 533–537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

* cited by examiner

METHOD FOR IMPROVING CARDIAC FUNCTION

CROSS-REFERENCE TO RELATED APPLICATIONS

The present patent application is a continuation application of prior U.S. patent application Ser. No. 10/212,032, filed on Aug. 1, 2002, which is a continuation-in-part application of prior U.S. patent application Ser. No. 09/635,511, filed on Aug. 9, 2000, now abandoned which claims priority from U.S. Provisional Patent Application No. 60/147,894 filed on Aug. 9, 1999, all of which are incorporated herein by reference in their entirety.

BACKGROUND OF THE INVENTION

1). Field of the Invention

This invention relates to a method and device for improving cardiac function.

2). Discussion of Related Art

Congestive heart failure annually leads to millions of hospital visits internationally. Congestive heart failure is a description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to an enlargement of the heart. A myocardial ischaemia may, for example, cause a portion of a myocardium of the heart to lose its ability to contract. Prolonged ischemia can lead to infarction of a portion of the myocardium (heart muscle) wherein the heart muscle dies and becomes scar tissue. Once this tissue dies it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way it is said to be dyskinetic. The dyskinetic portion of the myocardium may stretch and eventually form an aneurysmic bulge. Certain diseases may cause a global dilated myopathy, i.e., a general enlargement of the heart when this situation continues for an extended period of time. As the heart begins to fail, the filling pressures increase, which stretches the ventricular chamber prior to contraction, greatly increasing the pressure (preload) to the heart. In response, the heart tissue remodels to accommodate the chronically increased filling pressures, further increasing the work that the now-compromised myocardium must perform. This vicious cycle of cardiac failure results in the symptoms of congestive heart failure such as shortness of breath on exertion, edema in the periphery, nocturnal dypsnia (a characteristic shortness of breath that occurs at night after going to bed), weight gain, and fatigue, to name a few. The enlargements increase stress on the myocardium. The stress increase requires a larger amount of oxygen supply, which can result in exhaustion of the myocardium leading to a reduced cardia output of the heart.

SUMMARY OF THE INVENTION

According to one aspect of the invention, a method for improving cardiac function is provided. A membrane is inserted into a ventricle of the heart. The membrane is mounted in a position in the ventricle to substantially form a division between volumes of the ventricle on opposing sides of the membrane.

BRIEF DESCRIPTION OF THE DRAWINGS

The invention is further described by way of examples with reference to the accompanying drawings, wherein.

DETAILED DESCRIPTION OF THE INVENTION

Figure 1A:
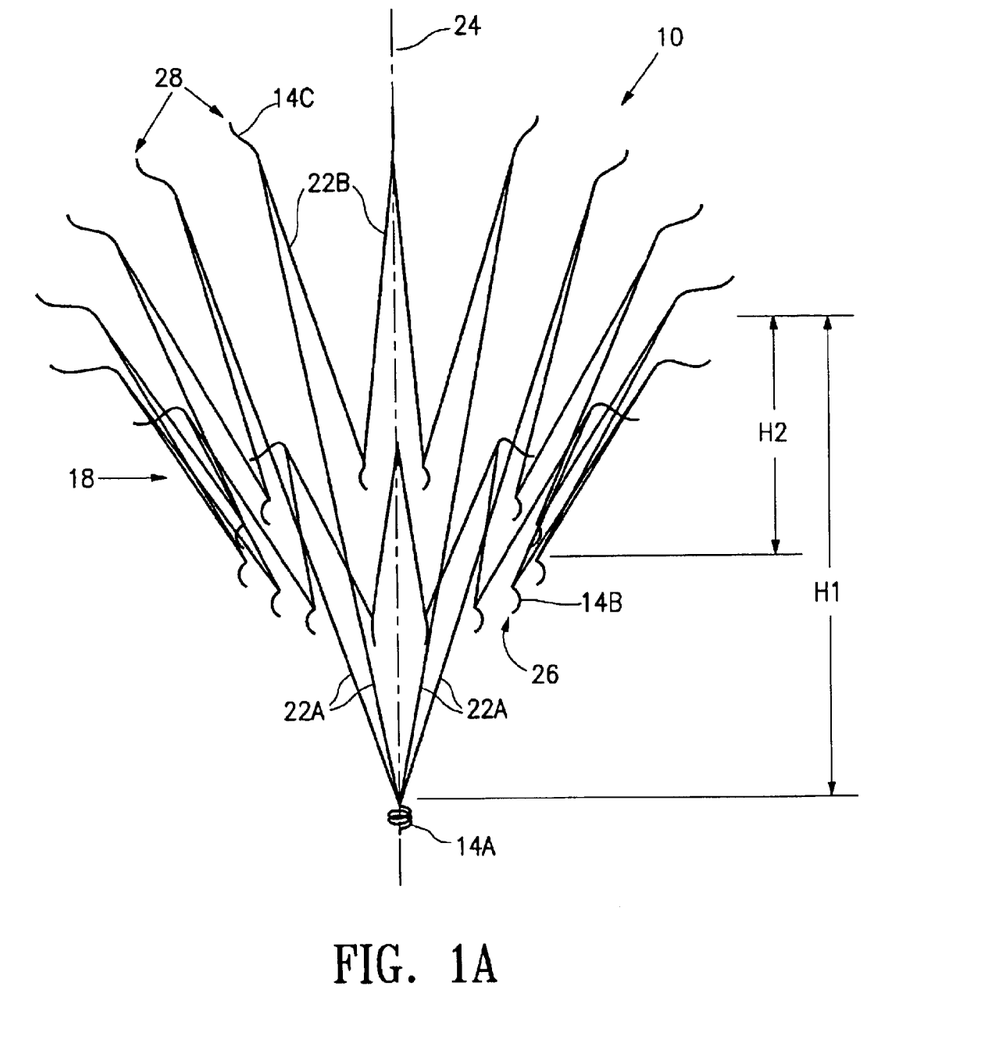
FIG. 1A is a perspective view of a main frame of a device, according to an embodiment of the invention, for improving cardiac function.
Figure 1B:
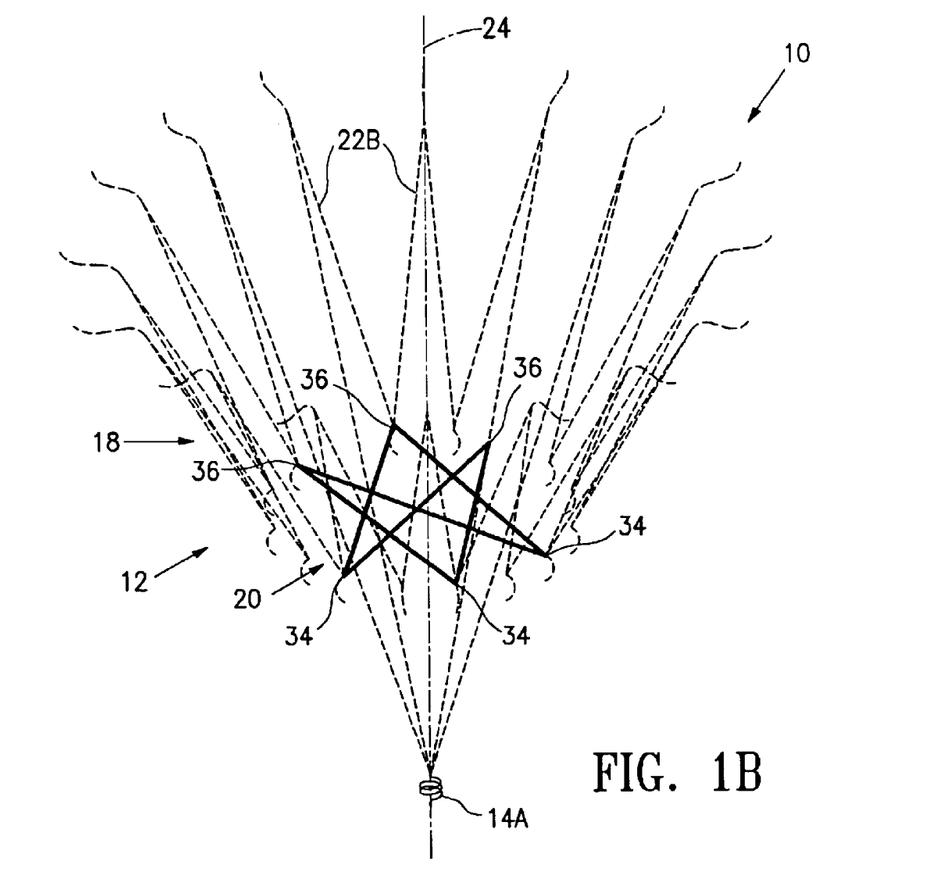
FIG. 1B is a view similar to FIG. 1A, illustrating the main frame in hidden lines and further illustrating in solid lines a support frame of the device mounted to the main frame.
Figure 1C:
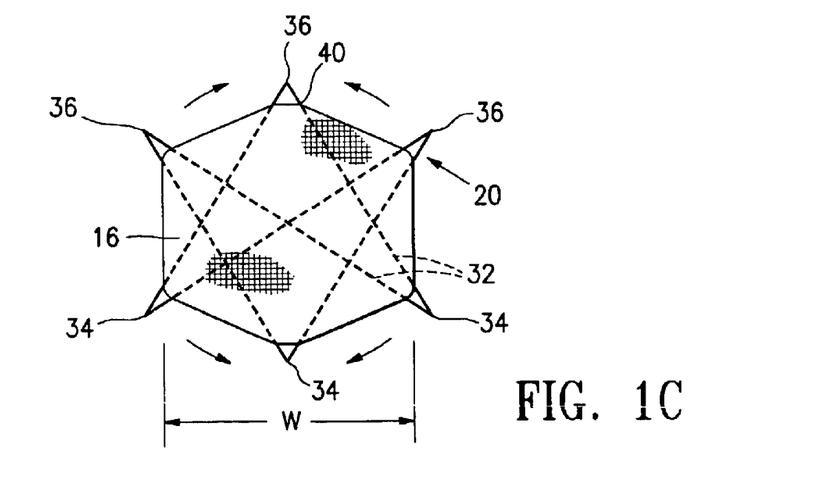
FIG. 1C is a top plan view illustrating a membrane of the device secured on top of the support frame.

FIGS. 1A, 1B, and 1C illustrate components of a device 10, according to an embodiment of the invention, for improving cardiac function. The device 10 includes a frame construction 12, a plurality of anchoring formations 14, and a membrane 16. The frame construction 12 includes a main frame 18 and a support frame 20 secured to the main frame 18. The membrane 16 is secured on top of the support frame 20.

As shown in FIG. 1A, the main frame 18 includes a sequence or series of segments 22. Even segments of the series extend in an upward direction, and odd segments extend downward. The sequence formed by the segments 22 entirely surrounds a vertical axis 24. Movement of the segments 22 toward one another causes collapse of the main frame 18 toward the vertical axis 24. The frame construction 12 is made of a biocompatible wire-like shape-memory material, for example, nickel-titanium.

The anchoring formations 14 include a distal anchoring screw 14A, distal anchoring hooks 14B, and proximal anchoring hooks 14C. Two or more (in the present example, four) of the segments 22A are longer, and extend further down than other ones of the segments 22B. The segments 22A have their lower ends connected to one another, and the distal anchoring screw 14A is secured to the lower ends of the segments 22A. The segments 22A and 22B may be curved, as opposed to being straight, as shown in the figures.

The distal anchoring hooks 14B are secured to lower ends of the segments 22B. Each distal anchoring hook 14B curves out and then down and is formed with a lower sharp end 26.

The proximal anchoring hooks 14C are secured to upper ends of the segments 22A and 22B. Each one of the proximal anchoring hooks 14C curves out and then up and terminates in an upper sharp end 28. The anchoring hooks 14B and 14C move together with the main frame 18 toward the vertical axis 24 when the main frame 18 is collapsed.

As shown in FIG. 1C, the support frame 20 includes six (or more) elements 32, sequentially after one another and overlaying one another to form a six-pointed star. The elements 32 can pivot in a scissor-like manner relative to one another. Pivoting of the elements 32 relative to one another moves corners 34 of the star toward one another, while corners 36 on an opposing side of the star move toward one another. The support frame 20 then has an elongated configuration with the corners 36 at one end and the corners 34 at an opposing end.

Referring to FIG. 1B, each corner 36 is positioned around and slidably secured to a respective one of the segments 22B. When the main frame 18 is collapsed, the corners 34 slide up the segments 22B to which they are secured, while the corners 36 remain at the bottom of the segments 22B to which they are secured. When the main frame 18 is fully collapsed, the support frame 20 is in the form of an elongated arrangement extending along the vertical axis 24, with the corners 34 at the top and the corners 36 at the bottom.

FIG. 1C also shows the membrane 16, in an unfolded condition, secured on the elements 32 of the support frame 20. An edge 40 of the membrane 16 is secured to the elements 32. Two of the elements 32 form a cross below a center of the membrane 16, and the other four elements 32 support the membrane 16 between the cross and the edge 40. Collapse of the support frame 20 folds the membrane 16 into an elongated folded arrangement extending along the elongated arrangement formed by the collapsed support frame 20. The membrane 16 is made of a biocompatible foldable material, for example Gore-Tex®, poly-ethylene terephthalate, or polypropylene mesh.

Figure 2A:
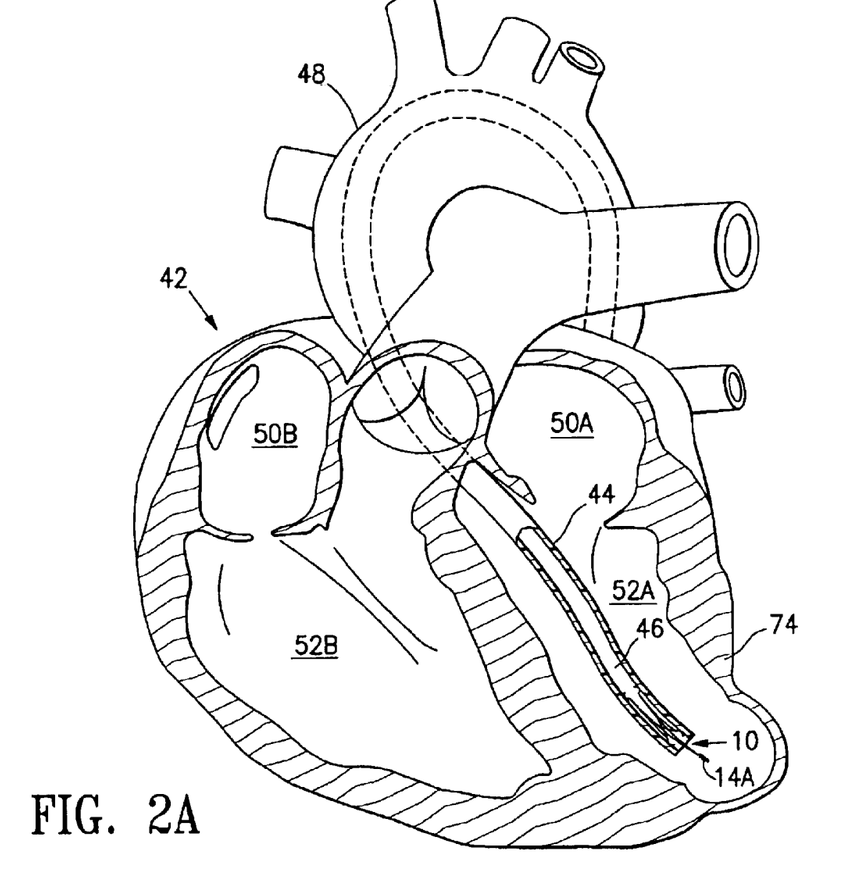
FIG. 2A is a cross-sectional side view of a heart, a catheter that is inserted into a left ventricle of the heart, and the device as it is packaged within an end of the catheter.

FIG. 2A illustrates the device 10 that is inserted into a heart 42 by means of a catheter 44. The device 10 is collapsed and is inserted into an end of the catheter 44. The axis 24, shown vertically in FIGS. 1A and 1B, now extends along an axis of an elongated tubular passage 46 in the catheter 44. The device 10 is packaged with the distal anchoring screw 14A protruding from the end of the catheter 44. The catheter 44 is non-invasively steered through the aorta 48 and the aortic valve (not shown) into the left ventricle 52A of the heart 42. The other chambers of the heart 42 are the right ventricle 52B, the left atrium 50A, and the right atrium 50B.

Figure 2B:
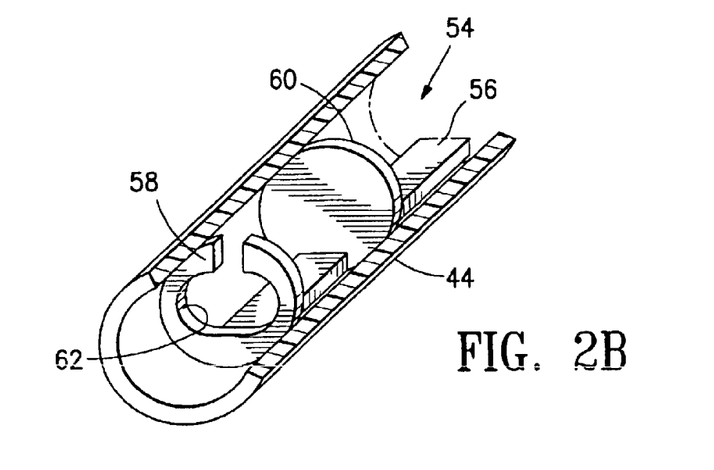
FIG. 2B is a perspective view illustrating a device manipulating apparatus within the end of the catheter.

As shown in FIG. 2B, a device manipulating apparatus 54 is disposed within the catheter 44. The apparatus 54 includes an elongated manipulator 56, a rotator piece 58, and a support piece 60. Only a distal portion of the elongated manipulator 56 is shown. A handle (not shown) is attached to a proximal portion of the elongated manipulator 56. The elongated manipulator 56 can bend to conform to the curved or bent shape of the catheter 44, but is relatively rigid against a torque about an elongated axis thereof. The rotator piece 58 is secured to an end of the elongated manipulator 56, and the support piece 60 is secured to the elongated manipulator 56 slightly proximal to the rotator piece 58. The rotator piece 58 has an internal device engaging formation 62. The device 10 is inserted into the formation 62 until proximal surfaces of the device 10 contact the support piece 60. The formation 62 conforms to an outer shape of the device 10, so that the device 10 rotates together with the rotator piece 58 when the rotator piece 58 is rotated by the elongated manipulator 56. The device 10 may be fed out of an end of the catheter 44 by the support piece 60 when the elongated manipulator 56 is advanced in an elongated direction of the catheter 44. The support piece 60 also prevents movement of the device 10 in an opposite direction into the catheter 44.

Figure 3A:
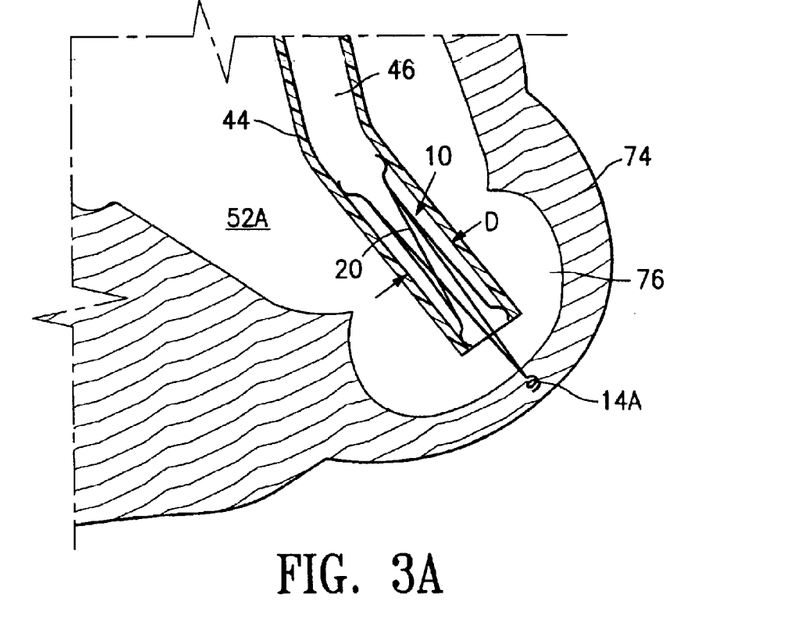
FIGS. 3A–3D illustrate how the device is secured to a myocardium of the heart.

Reference is now made to FIG. 3A. The myocardium 74 of the heart has formed an aneurysmic formation or bulge 76 out of the left ventricle 52A. A previous infarction, or cessation of blood supply, to the portion of the myocardium 74 now forming the bulge 76 has caused the tissue of that portion of the myocardium 74 to die. Continuous exposure of the dyskinetic portion of the myocardium 74 to high pressures in the left ventricle 52A has caused the aneurysmic bulge 76.

The catheter 44 is steered so that the distal anchoring screw 14A contacts a base of the bulge 76. The catheter 44 is then rotated so that the distal anchoring screw 14A screws into the myocardium 74 at a target site at the base of the bulge 76.

Figure 3B:
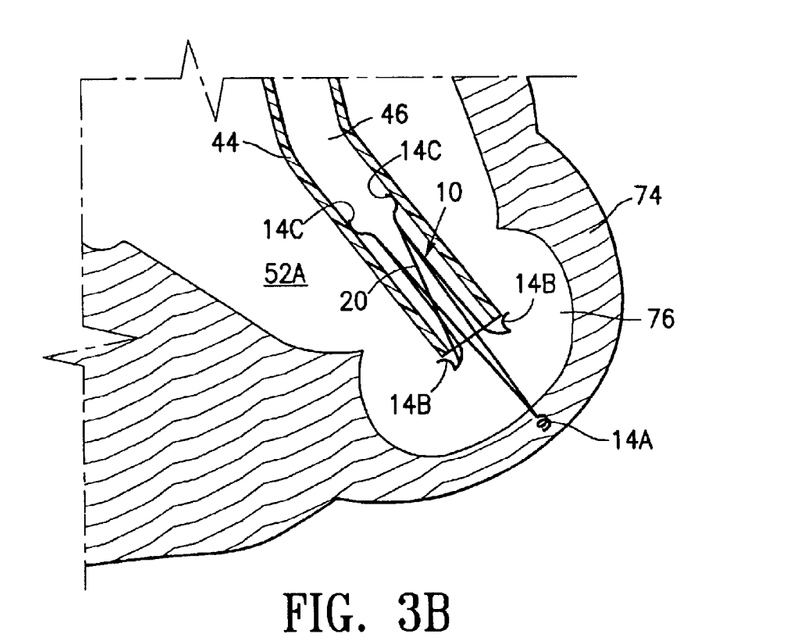

As shown in FIG. 3B, the catheter 44 is then retracted over the device 10 with the distal anchoring screw 14A anchoring the frame construction 12 to the myocardium 74 at the base of the bulge 76. The distal anchoring hooks 14B leave the catheter 44 as the catheter 44 is retracted, before the remainder of the device 10, and bend outwardly under spring action.

Figure 3C:
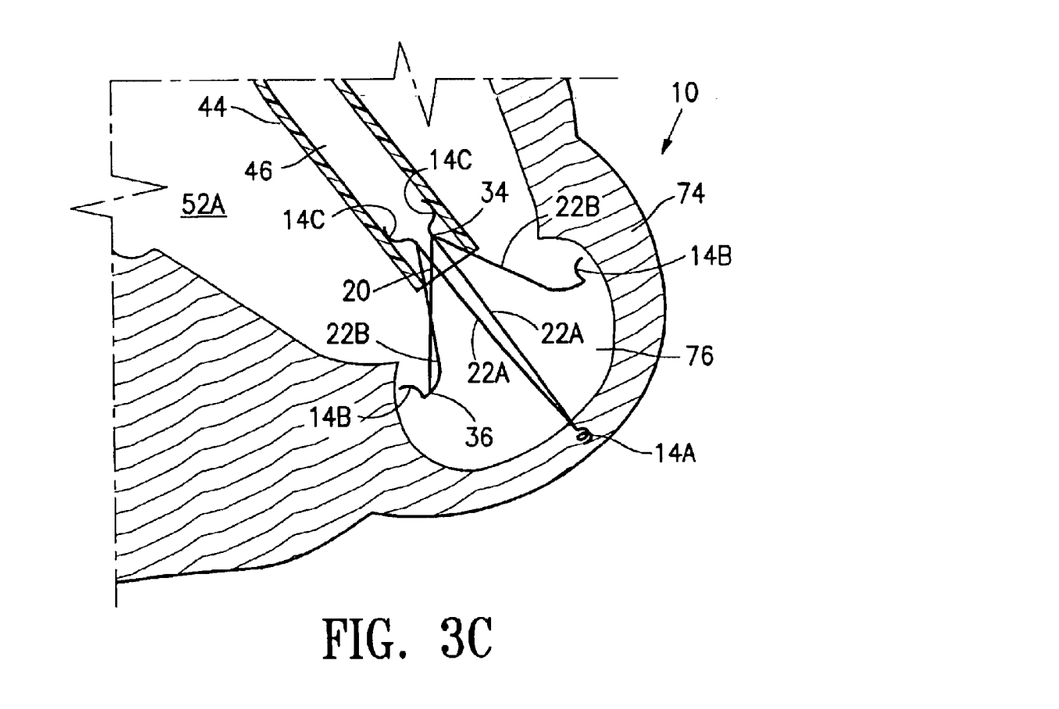

As shown in FIG. 3C, further withdrawal of the catheter 44 from the segments 22B causes the segments 22B to spring outwardly, and the distal anchoring hooks 14B to come into contact with the myocardium 74. The support frame 20 pivots away from its alignment with the center axis of the elongated tubular passage 46, and the proximal anchoring hooks 14C are at this stage still located within the elongated tubular passage 46.

Figure 3D:
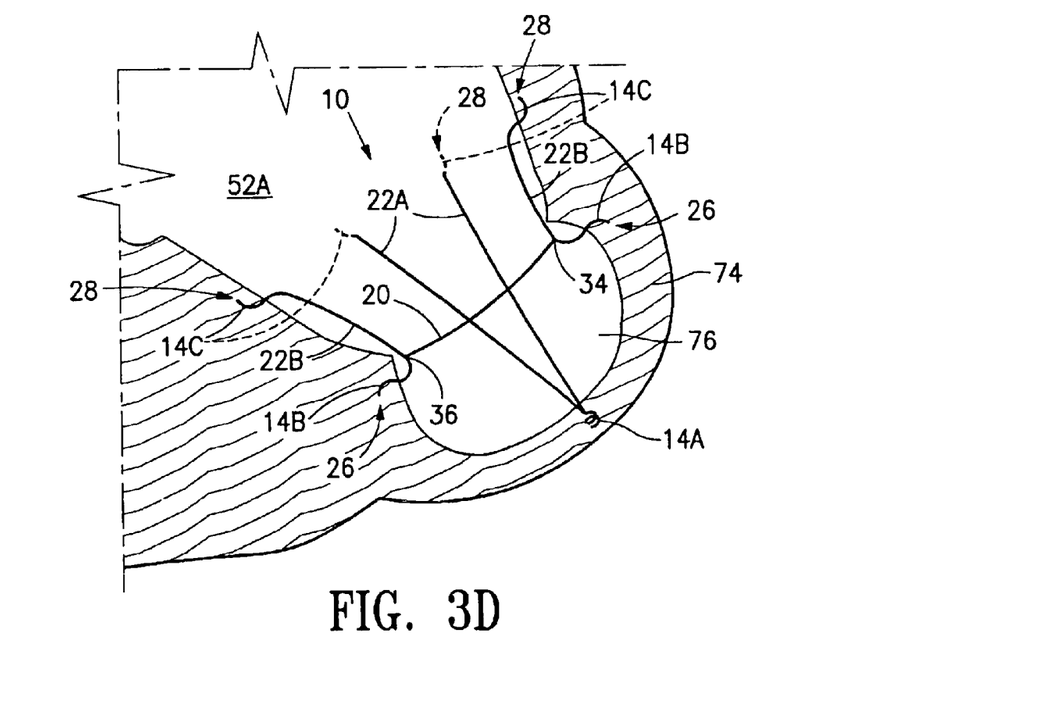

As shown in FIG. 3D, the catheter 44 is subsequently withdrawn from proximal anchoring hooks 14C. Proximal portions of the segments 22A and 22B spring outwardly after the proximal anchoring hooks 14C leave the tubular passage 46, so that the proximal anchoring hooks 14C move outwardly into contact with the myocardium 74. A proximal portion of each segment 22A or 22B pivots relative to a distal portion thereof. Pivoting of the segments 22B rotates the lower sharp ends 26 of the distal anchoring hooks 14B into the myocardium 74. Embedding of the distal anchoring hooks 14B into the myocardium 74 anchors the segments 22B to the myocardium 74. Beating of the heart 42 causes relative movement between the myocardium 74 and proximal anchoring hooks 14C, so that the upper sharp ends 28 may also penetrate the myocardium 74. The proximal anchoring hooks 14C are thereby also embedded into the myocardium 74, and anchor proximal portions of the segments 22A and 22B to the myocardium 74. Each segment 22A or 22B is near the myocardium 74 at all locations along the length of the respective segment 22A or 22B, and is anchored to the myocardium 74 through the anchoring formations 14.

The corners 34 of the support frame 20 slide along the segments 22B to which they are secured when the segments 22B rotate outwardly relative to one another. When comparing FIG. 3D with FIG. 3C, it can be seen that the support frame 20 is in a plane which is substantially at right angles with respect to the axis of the elongated tubular passage 46. The membrane 16 (FIG. 1C) unfolds and is supported on top of the support frame 20. The membrane 16 forms a division between the aneurysmic bulge 76 and a remainder of the left ventricle 52A.

After the device 10 is installed, the aneurysmic bulge 76, having been segregated from the remainder of the left ventricle 52A, eventually clots off behind the sheet 16, thereby effectively reducing the internal volume in the left ventricle 52A. Stretching of the portion of the myocardium 74 forming the aneurysmic bulge 76 is also effectively eliminated. By blocking off a portion of the left ventricle 52A not contributing to pumping during a systolic portion of a pump cycle, properly functioning portions of the myocardium 74 can contract normally and use up a normal amount of oxygen. By reducing the amount of oxygen up take during a given period of time, properly functioning portions of the myocardium 74 are not exhausted and can continue to function properly. Cardiac output increases, and the likelihood of congestive heart failure is reduced, assuming that all other conditions remain the same. A reduction in the strength of the contractions of the properly functioning portions of the myocardium also reduces LVESP, with a corresponding reduction in stress of both dyskinetic and properly functioning portions of the myocardium 74.

Figure 4A:
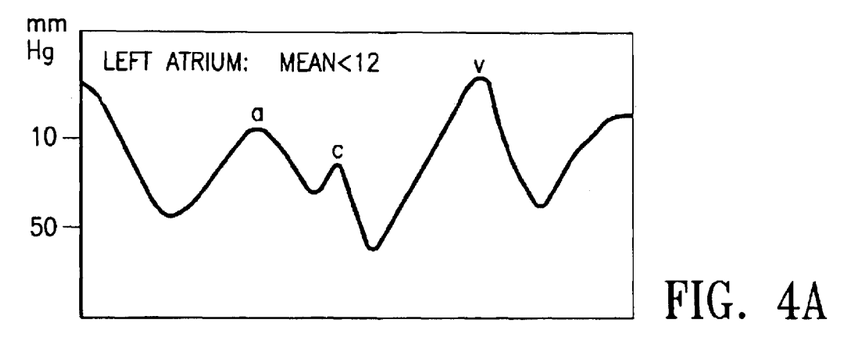
FIGS. 4A–4B are graphs illustrating the pressures within the left atrium and the left ventricle, respectively.
Figure 4B:
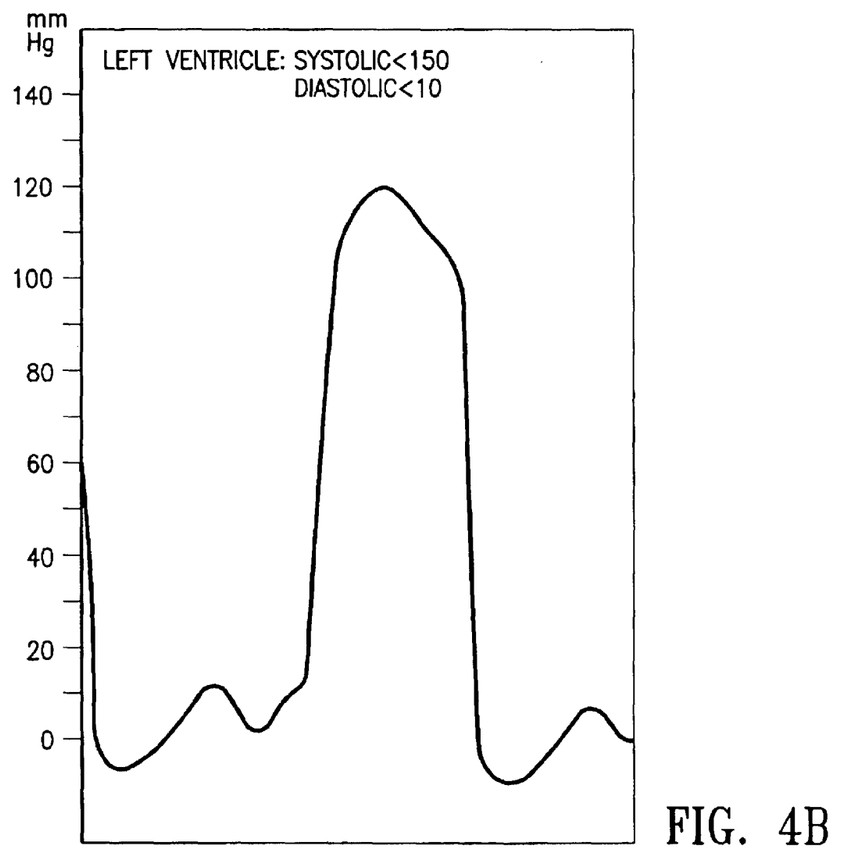

FIGS. 4A and 4B illustrate pressures within the left atrium 50 and the left ventricle 52A, respectively, of a healthy human being. It can be seen that the peak left ventricular pressure, i.e., the pressure in the left ventricle 52A during the systolic portion, reaches approximately 120 mm Hg. This pressure acts directly on the membrane 16. It can be assumed that the pressure on an opposing side of the membrane 16, i.e., the side of the aneurysmic bulge 76, is close to zero. The support frame 20 supports the sheet 16 at a sufficient number of locations and is sufficiently strong to prevent the membrane 16 from collapsing during peak systolic pressure. A peak left ventricular pressure in the region of 50 to 60 mm Hg for a sustained period of a few hours is generally regarded as being incompatible with life.

In the given example, there are a total of 31 anchoring formations 14, including the distal anchoring screw 14A, 14 distal anchoring hooks 14B, and 16 proximal anchoring hooks 14C. The large number of anchoring formations 14 ensure proper anchoring to the myocardium 74. The large number of anchoring formations 14 also allows for positioning of the membrane 16 at a select location within the left ventricle 52A and at a select angle and within a select plane relative to the myocardium 74. The anchoring formations 14, and in particular the anchoring hooks 14B and 14C, their shape, orientation, and placement, are thus uniquely suited for anchoring of the frame construction 12, especially when compared with other anchoring formations such as pins, clamps, staples, screws, and surgical thread. What should also be noted is that the anchoring formations 14 penetrate through only a portion of the myocardium 74, and thus do not damage the pericardium. What should further be noted is that none of the anchoring formations 14 or other components of the device 10 can bump against the myocardium 74, to avoid electrostimulation of the myocardium 74 that can lead to arrhythmias.

Figure 5A:
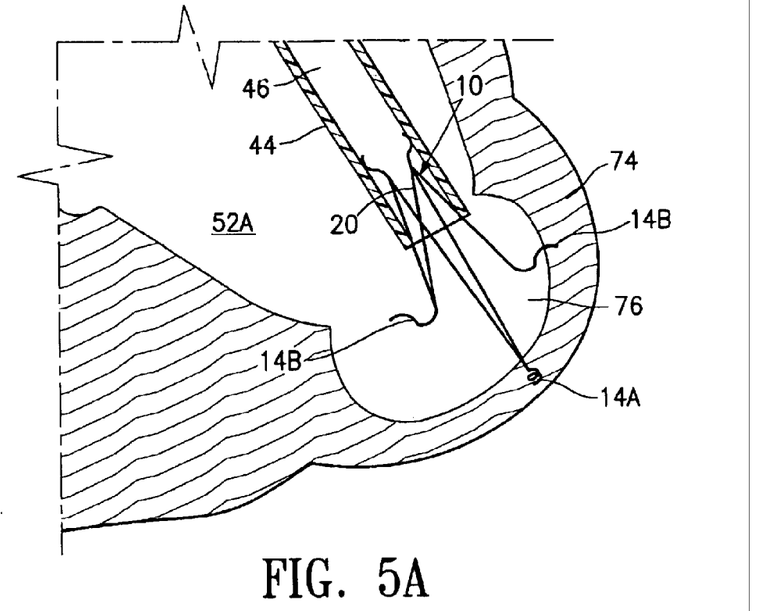
FIGS. 5A–5C illustrate how the device can be mounted with the support frame to support the membrane in a different plane.
Figure 5B:
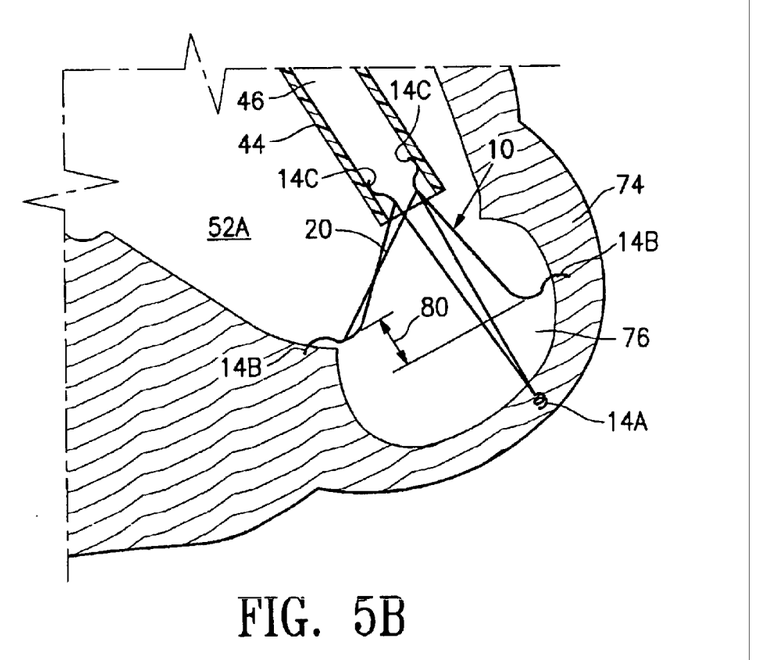
Figure 5C:
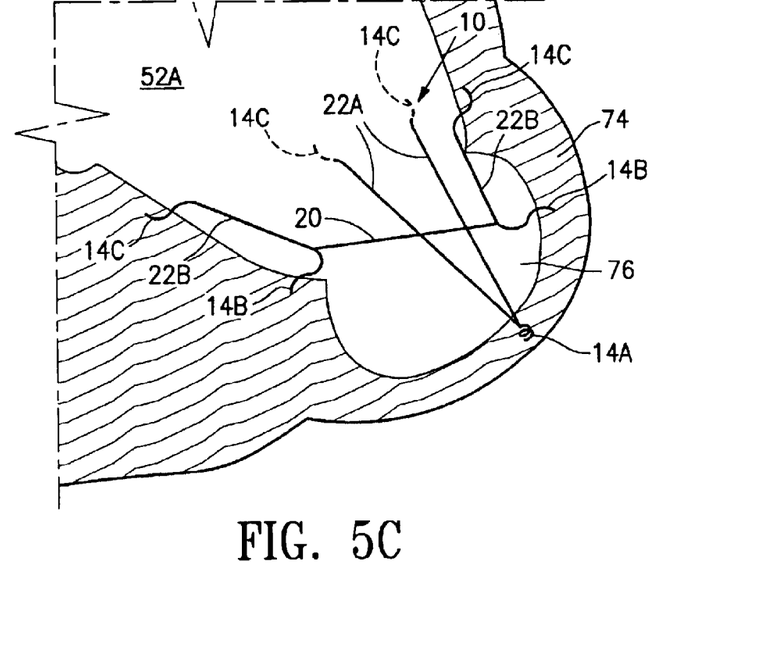

FIGS. 5A, 5B, and 5C illustrate one manner in which the support frame 20 and the membrane 16 can be positioned at a select angle relative to the myocardium 74. When comparing FIG. 5A with FIG. 3C, it can be seen that the catheter 44 is positioned closer to a right side (as viewed) of the myocardium 74. The distal anchoring hooks 14B on the right engage with the myocardium 74 before the distal anchoring hooks 14B on the left engage with the myocardium 74. Further withdrawal of the catheter 44, as shown in FIG. 5B, results in engagement of the distal anchoring hooks 14B on the left with the myocardium 74 at a location which is displaced by an offset distance 80 in a direction of an axis of the elongated tubular passage 46. When comparing FIG. 5C with FIG. 5B, it can be seen that, due to the offset distance 80, the support frame 20 is eventually at an angle of approximately 60° relative to the axis of the elongated tubular passage 46. Although not blocking a mouth of the aneurysmic bulge 76, this serves to illustrate that the membrane 16 can be positioned in different select planes, as may be required, due to the flexibility of the frame construction 12 and various virtual triangles that are formed by connecting locations where the anchoring formations 14 anchor to the myocardium 74.

Referring again to FIGS. 1A, 1C, and 3A, the main frame 18 has a vertical height H1, a height from the distal anchoring hooks 14B to the proximal anchoring hooks 14C H2, the membrane 16 has a width W, and the elongated tubular passage 46 has a diameter D. These dimensions can be modified according to requirement, and the following table lists a number of examples:

| H1 | H2 | W | D |
|---|---|---|---|
| 6 cm | 3 cm | 2.5 cm | 1 cm |
| 7 cm | 4 cm | 3 cm | 1.2 cm |
| 8 cm | 5 cm | 4 cm | 1.5 cm |
| 8.5 cm | 5.5 cm | 5 cm | 2 cm |
| 9.5 cm | 6 cm | 6 cm | 2.2 cm |
| 9.5 cm | 8 cm | 7 cm | 2.6 cm |

The first row in the table lists the dimensions for the device 10 hereinbefore described which is used for blocking a relatively small aneurysmic bulge 76. Larger aneurysmic bulges can be blocked using slightly larger devices. As mentioned, certain diseases or alcoholism may cause general enlargement of endocardial cavities of a heart without necessarily creating a specific identifiable bulge. Larger devices can be used to block portions of these enlarged endocardial cavities. In such cases, it may also be possible to use two devices in a side-by-side arrangement or with their membranes overlapping one another.

Figure 6:
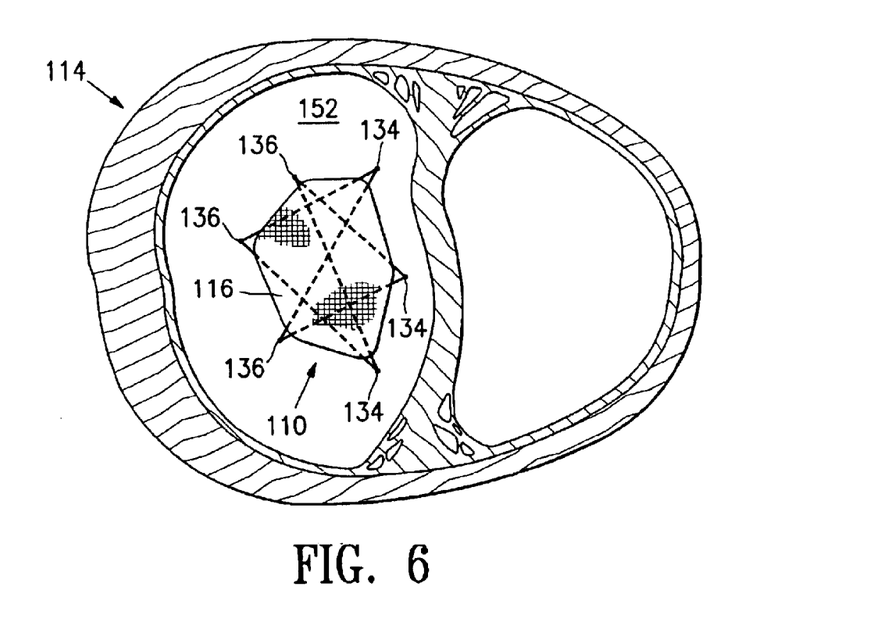
FIG. 6 is a top plan view illustrating a larger device, according to another embodiment of the invention, mounted in a lower portion within a left ventricle of a heart.

FIG. 6 illustrates one such a larger device 110 that is inserted in the bottom of the left ventricle 152 of a heart 114. The main frame (not shown) of the device 110 is formed into a non-circular shape, so that an outline formed by corners 134 and 136 of a support frame of the device define a non-circular shape. A membrane 116 mounted on top of the support frame also defines a non-circular shape. The shape of the membrane 116 conforms approximately to a non-circular D-shape of the left ventricle 152 at a height where the membrane 116 is positioned. The same device 110 can be deformed into various different shapes, according to requirement.

Figure 7A:
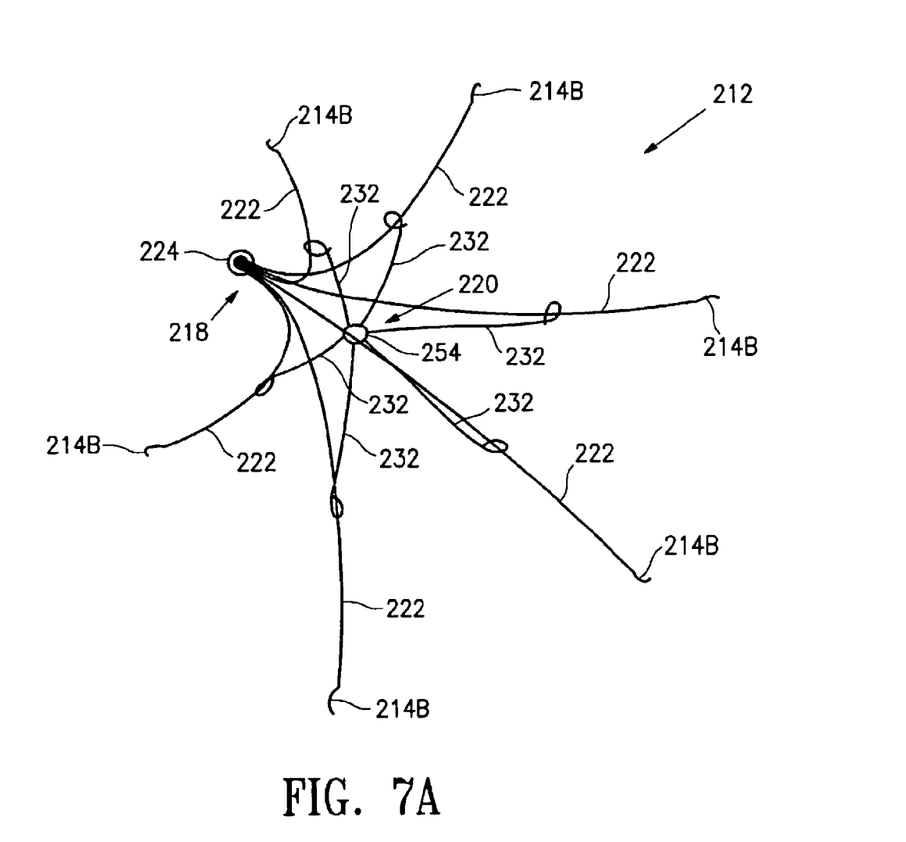
FIGS. 7A–7B are perspective views from different sides, illustrating components of a device according to a further embodiment of the invention.
Figure 7B:
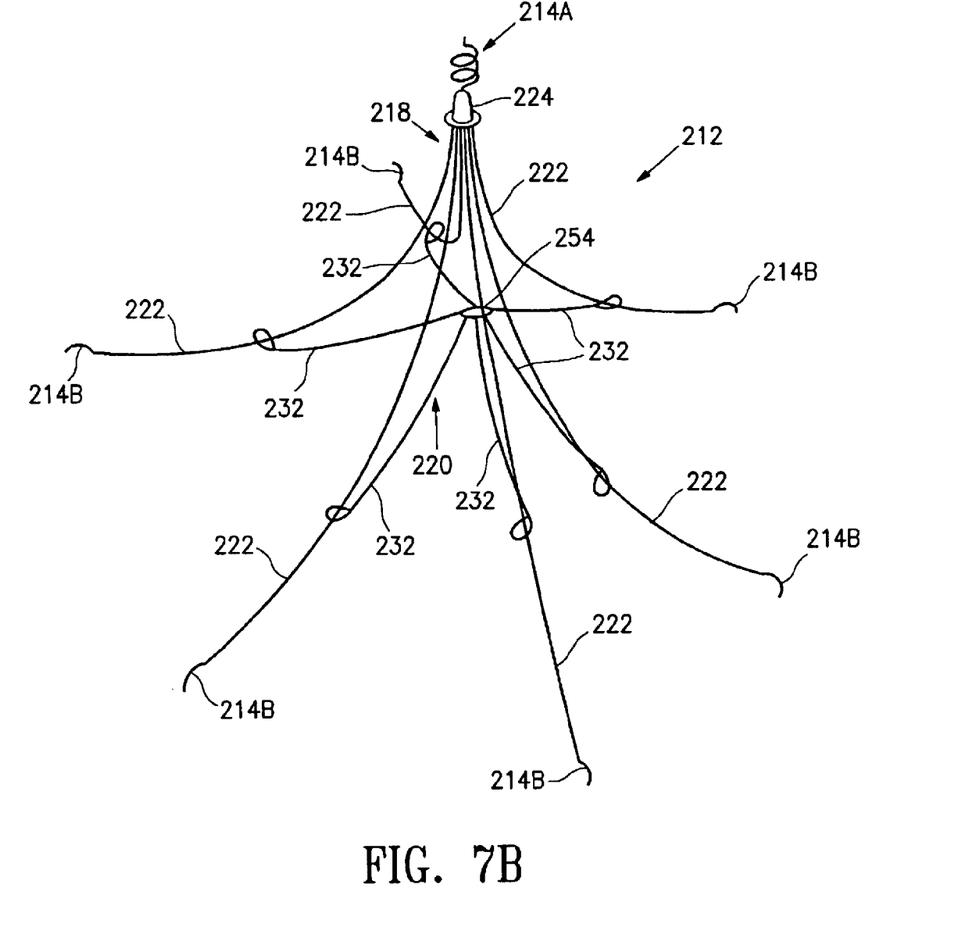

FIGS. 7A and 7B illustrate a frame construction 212 and anchoring formations 214 of a device according to an alternative embodiment of the invention. The frame construction 212 includes a main frame 218 and a support frame 220. The main frame 218 has a plurality of segments 222 having distal ends connected to one another at a common location 224. Proximal portions of the segments 222 can collapse toward one another and spring outwardly away from one another. The anchoring formations 214 include a distal anchoring screw 214A secured at the common location 224, and proximal anchoring hooks 214B on proximal ends of the segments 222. The support frame 220 includes a plurality of elements 232. The elements 232 have ends that are pivotally connected to one another at a common location 254. An opposing end of each element 232 is slidably secured to a respective one of the segments 222. The manner in which the segments 222 of the main frame 218 collapse is simultaneously replicated by the manner in which the elements 232 of the support frame 220 collapse. In use, the distal anchoring screw 214A is first screwed into a myocardium. A catheter is then withdrawn from the frame construction 212. Once the catheter is entirely removed from the frame construction 212, the proximal anchoring hooks 214B spring outwardly and embed themselves into the myocardium. The support frame 220 simultaneously moves from its collapsed condition into its expanded condition. A membrane (not shown) is secured to, unfolded by, and supported by the support frame 220.

Figure 8:
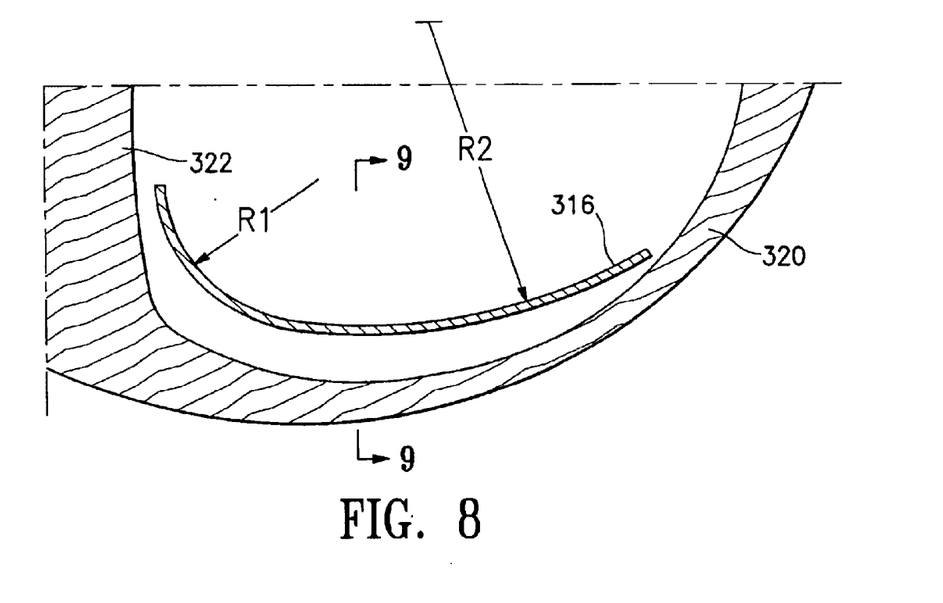
FIG. 8 is a cross-sectional side view illustrating a sheet that is curved to substantially conform to an inner wall of a heart.
Figure 9:
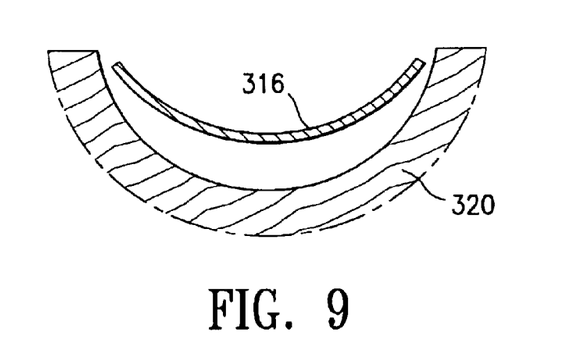
FIG. 9 is a cross-sectional end view on 9—9 in FIG. 8.

The support frame of a device may be shaped so that a membrane attached to the support frame has a desired shape. FIGS. 8 and 9, for example, illustrate a membrane 316 that conforms approximately to a shape defined by an anterior wall 320 and a septum 322 of a heart. As shown in FIG. 8, the membrane 316 has a portion on the left having a radius R1 and a portion on the right having a radius R2 which is a multiple of the radius R1. The membrane 316 may be formed to have more than two radii of curvature. Referring to FIG. 9, it can be see that the membrane 316 is curved also when viewed on 9—9 in FIG. 8. The curved shape of the membrane 316 allows the membrane 316 to block off larger portions of the anterior wall 320 and the septum 322 without reducing the internal volume of the left ventricle by too great a degree.

Figure 10:
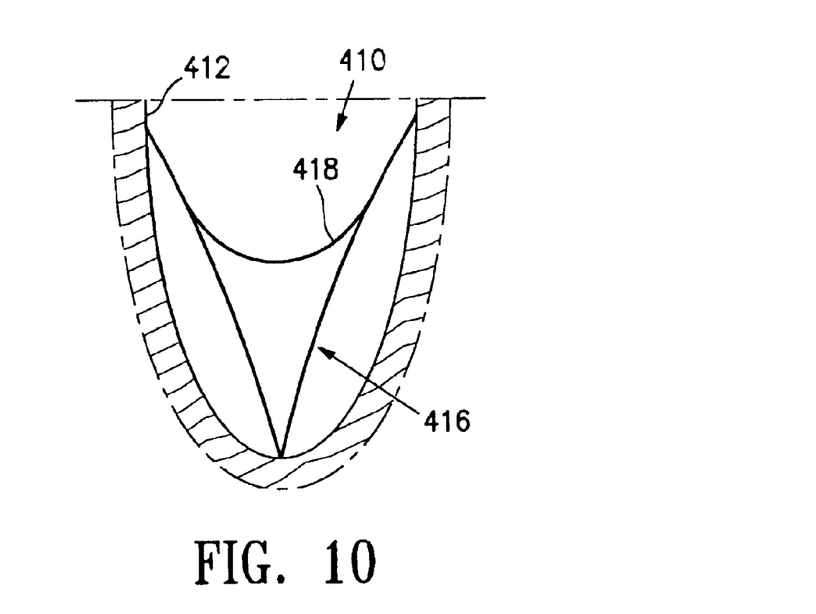
FIG. 10 is a cross-sectional side view illustrating a device that is used for closing off a small ventricle of a heart.
Figure 11:
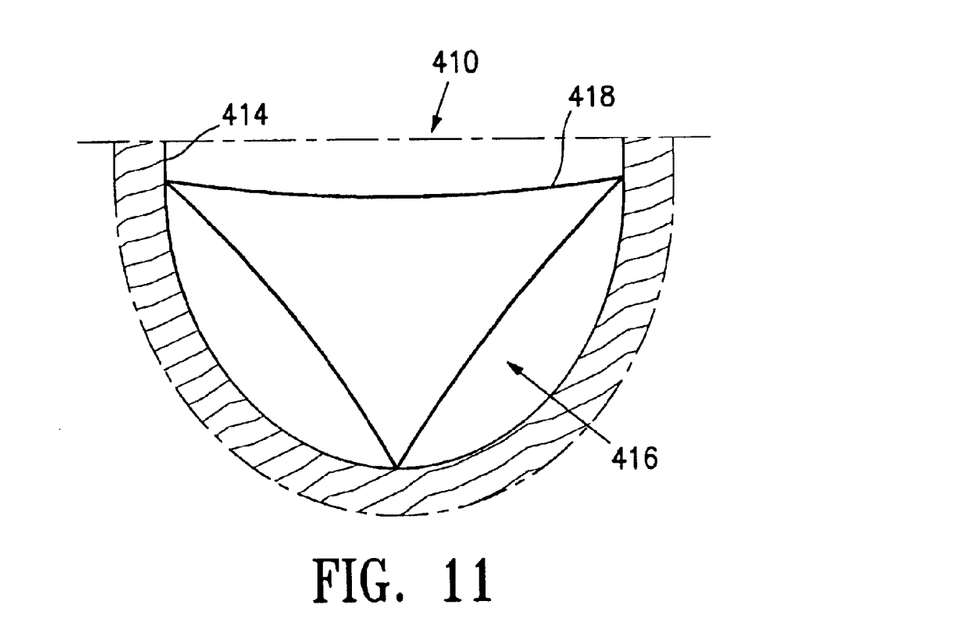
FIG. 11 is a cross-sectional side view illustrating the same device as in FIG. 10, used for closing off a large ventricle of a heart.

It may also be possible to use the same device to block off either large or small cavities. FIGS. 10 and 11 illustrate the same device 410 used for closing off a small ventricle 412 and a large ventricle 414, respectively. As in, for example, the embodiment described with reference to FIGS. 7A and 7B, the device 410 has a frame construction 416 that can spring outwardly, and a membrane 418 secured and expanded by the frame construction 416. The frame construction 416 springs out more in FIG. 11 than in FIG. 10, and the membrane 416 is accordingly unfolded into a larger cross-sectional shape.

The support frame and anchoring formations of, for example, the device illustrated in FIG. 1A may be used for other purposes instead of or in addition to supporting a membrane as described. The frame construction 18 provides an electrically conductive path that can be used for left ventricular pacing. For example, one of the proximal anchoring hooks 14C may engage with and be sufficiently long to penetrate from a left ventricle through a septum into a right ventricle of a heart. A terminal of a pacemaker can then be inserted into the right ventricle and connected to the hook that penetrates through the septum. Electric current can conduct between the terminal of the pacemaker through the main frame 18 to other ones of the anchoring formations 14 connected to the myocardium of the left ventricle. The frame construction 12 also provides a strong support for mounting components that can be used for other purposes, such as an annulus component that can be positioned around the mitral valve, or a component that is used for reshaping a papillary muscle. The device 10 can also be used for delivering of drugs, proteins, stem cells, etc. to the heart.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A method of treating a patient's with congestive heart failure, comprising:

advancing a reinforced partitioning component into a left ventricle of the patient's heart in a contracted configuration;

expanding the reinforced partitioning component within the left ventricle to a deployed configuration;

securing a periphery of the expanded reinforced partitioning component within the left ventricle of the patient's heart to separate the left ventricle into a main functioning portion and a secondary, essentially non-functioning portion with a central portion of the partitioning component spaced from a ventricular wall of the secondary portion of the patient's left ventricle.

2. The method of claim 1, wherein at least a peripheral part of the reinforced partitioning component penetrates into but not through a ventricular wall defining in part the left ventricle.

3. The method of claim 2, wherein the peripheral part of the reinforced partitioning component that penetrates into but not through a ventricular wall is an anchoring hook having a sharp penetrating end.

4. The method of claim 3, wherein the sharp penetrating end is at least one of a pin, a clam, a staple, a screw, and surgical thread.

5. The method of claim 1, wherein the periphery of the reinforced partitioning component is secured at a plurality of locations.

6. The method of claim 1, wherein anchoring the expanded reinforced partitioning component within the left ventricle increases cardiac output of the heart.

7. The method of claim 1, wherein the the expanded reinforced partitioning component within the left ventricle decreases myocardium stretch during a pump cycle of the left ventricle.

8. The method of claim 1, wherein the left ventricle sustains a peak left ventricular pressure above 60 mm Hg.

9. The method of claim 8, wherein the peak left ventricular pressure is approximately 120 mm Hg.

10. A method of treating a patient having congestive heart failure, comprising:

percutaneously introducing a delivery catheter into the patient's vasculature and advancing the delivery catheter therein until a distal end of the delivery catheter is disposed within the patient's left ventricle;

advancing a reinforced partitioning membrane device through the delivery catheter until the reinforced partitioning membrane device is discharged into an left ventricle of the patient's heart;

expanding the reinforced partitioning membrane device at a location within the patient's left ventricle to partition the patient's left ventricle into pressurized and non-pressurized portions; and anchoring the expanded reinforced partitioning membrane device at the location.

11. The method of claim 10 wherein the reinforced partitioning membrane is a porous membrane.

12. The method of claim 11 wherein the membrane partitions the heart chamber into pressurized and non-pressurized portions.

13. A method of improving cardiac function of a patient's heart, comprising:
   a. providing a reinforced membrane device configured to be secured within a portion of a left ventricle of the patient's heart;
   b. anchoring the reinforced membrane device within the patient's left ventricle to partition the left ventricle into pressurized and unpressurized portions to improve the cardiac function of the heart, and
   c. axially spacing a central portion of the reinforced membrane device from a wall defining at least in part the un-pressurized portion of the left ventricle.

14. The method of claim 13 wherein the central portion of the reinforced membrane device has a stem extending from the central portion thereof to space the central portion from the wall defining at least in part the un-pressurized portion of the left ventricle.

15. The method of claim 14, wherein the the stem of the reinforced partitioning component includes a screw at a free end to secure the stem to the ventricular wall of the secondary portion of the patient's left ventricle.

16. The method of claim 13 wherein the reinforced membrane partitioning component has a stem extending from the central portion thereof to space the central portion from the wall of the secondary portion of the patient's left ventricle.

* * * * *